(12) United States Patent
Van Hulle et al.

(10) Patent No.: US 8,611,995 B2
(45) Date of Patent: Dec. 17, 2013

(54) ENABLING DEVICE FOR IMPLANTABLE MEDICAL DEVICES

(75) Inventors: Koenraad Van Hulle, Rumst (BE); Koen Van den Heuvel, Hove (BE); Werner Meskens, Opwijk (BE)

(73) Assignee: Cochlear Limited (AU)

( * ) Notice: Subject to any disclaimer, the term of this patent is extended or adjusted under 35 U.S.C. 154(b) by 0 days.

(21) Appl. No.: 13/450,626

(22) Filed: Apr. 19, 2012

(65) Prior Publication Data

US 2013/0282067 A1    Oct. 24, 2013

(51) Int. Cl.
*A61N 1/00* (2006.01)

(52) U.S. Cl.
USPC .................................................... 607/2

(58) Field of Classification Search
USPC ........................................ 607/2, 60; 380/270
See application file for complete search history.

(56) References Cited

U.S. PATENT DOCUMENTS

| | | | |
|---|---|---|---|
| 4,676,248 A | 6/1987 | Berntson | |
| 4,955,729 A | 9/1990 | Marx | |
| 6,185,452 B1 | 2/2001 | Schulman et al. | |
| 6,804,554 B2 | 10/2004 | Ujhelyi et al. | |
| 6,917,831 B2 | 7/2005 | Bloemer et al. | |
| 7,024,249 B2 | 4/2006 | Weisner et al. | |
| 7,346,397 B2 | 3/2008 | Money et al. | |
| 7,890,743 B2 | 2/2011 | Buchanan et al. | |
| 2004/0039423 A1 | 2/2004 | Dolgin | |
| 2004/0138724 A1* | 7/2004 | Sieracki et al. | 607/60 |
| 2007/0297609 A1* | 12/2007 | Adams et al. | 380/270 |
| 2008/0123882 A1 | 5/2008 | Bauml et al. | |
| 2008/0207246 A1 | 8/2008 | Shanbhag et al. | |
| 2008/0300658 A1 | 12/2008 | Meskens | |
| 2010/0042177 A1 | 2/2010 | Stahmann et al. | |
| 2011/0046520 A1 | 2/2011 | Fricke et al. | |
| 2012/0271380 A1* | 10/2012 | Roberts et al. | 607/60 |

OTHER PUBLICATIONS

International Search Report and Written Opinion for PCT/IB2013/052936 mailed Sep. 6, 2013.

\* cited by examiner

*Primary Examiner* — Robert N Wieland
(74) *Attorney, Agent, or Firm* — McDonnell Boehnen Hulbert & Berghoff LLP

(57) ABSTRACT

Methods and devices for determining the operating mode of an implantable medical device are disclosed. A first device transmits a keep-alive signal to an implantable medical device. If the implantable medical device receives the keep-alive signal within a first time interval, the implantable medical device operates in a normal operating mode. If the implantable medical device does not receive the keep-alive signal with the first time interval, at least a portion of the implantable medical device is deactivated.

28 Claims, 6 Drawing Sheets

ENABLING DEVICE FOR IMPLANTABLE MEDICAL DEVICES

BACKGROUND

Individuals who suffer from certain medical conditions may benefit from the use of an implantable medical device. Depending on the type and the severity of the medical condition, an individual can employ a partially implantable medical device or a totally implantable medical device. Partially implantable medical devices typically include an external component that performs at least some processing functions and an implanted component that at least delivers a stimulus to a body part of a user, such as an organ. In the case of a totally implantable medical device, the entire device is implanted in the body of a user. Additionally, the implantable medical device is often configured to communicate with a remote device that allows an individual to adjust a component or a function of the implantable medical device.

SUMMARY

A method for determining an operating mode of an implantable medical device is disclosed. In one example, the method includes receiving a first transmission of a signal at the medical device. The method also includes starting a timer for a time interval in which the implantable medical device receives a second transmission of the signal. Upon determining that the implantable medical device did not receive the second transmission prior to the expiration of the timer, the method includes deactivating at least a portion of the implantable medical device.

A method for determining a number of missed signals in a sample interval is also disclosed. The number of missed signals includes a first number of time intervals in which the implantable medical device did not receive a signal. The sample interval includes a second number of time intervals in which the implantable medical device could have received the signal. The method also includes making a first determination in which the processor determines whether the number of missed signals is less than the first value. The first value represents a first allowable number of time intervals in which the implantable medical device did not receive the signal. Additionally, the method includes selecting an operating mode of the implantable medical device based on the first determination.

A system is also disclosed. The system includes a remote device configurable to transmit a signal. The system also includes an implantable medical device configured to receive the signal within a time interval. If the implantable medical device fails to receive the signal within the time interval, at least a portion of the implantable medical device is deactivated.

Additionally, an implantable medical device is disclosed. The implantable medical device includes a stimulating, an output component, a receiver, and processor. The processor makes a first determination of whether the receiver received the first signal in a first time interval. Based on the first decision, the processor sends a second signal to the output component that includes information indicating whether the output component sends an output signal to the stimulating component.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE FIGURES

Presently preferred embodiments are described below in conjunction with the appended drawing figures, wherein like reference numerals refer to like elements in the various figures, and wherein.

DETAILED DESCRIPTION

The following detailed description describes various features, functions, and attributes of the disclosed systems, methods, and devices with reference to the accompanying figures. In the figures, similar symbols typically identify similar components, unless context dictates otherwise. The illustrative embodiments described herein are not meant to be limiting. Certain aspects of the disclosed systems, methods, and devices can be arranged and combined in a wide variety of different configurations, all of which are contemplated herein.

Figure 1:
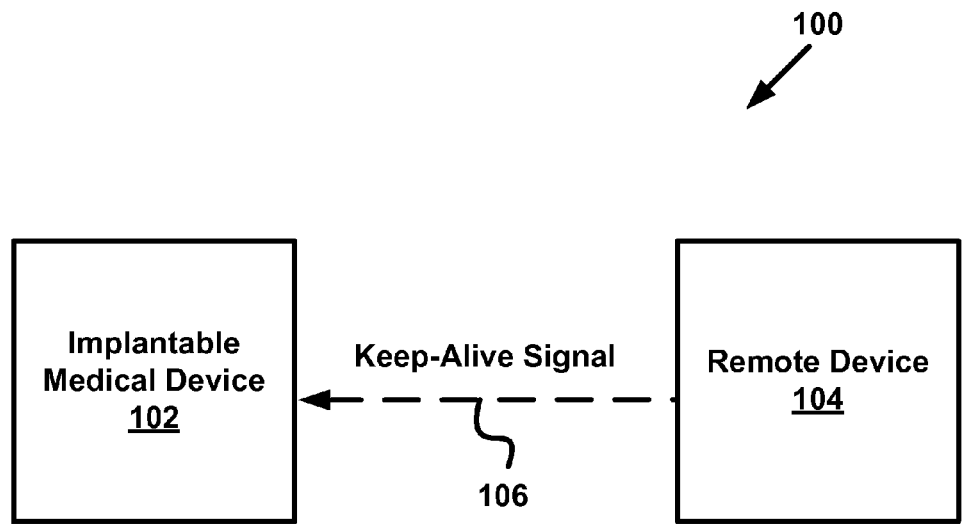
FIG. 1 is a block diagram of a communication system, according to an example.

FIG. 1 is a block diagram of a communication system 100. The communication system 100 includes an implantable medical device 102 and a remote device 104. The implantable medical device 102 receives a keep-alive signal 106 from the remote device 104.

The implantable medical device 102 is configured to stimulate an organ or a body part of a user. The implantable medical device may be totally implantable or partially implantable depending on a user's medical condition. In one example, the implantable medical device 102 is totally implantable, and the implantable medical device 102 is implanted in the user's body. In another example, the implantable medical device 102 is partially implantable, in which case a portion of the implantable medical device 102 is externally attached to the user's body.

If the implantable medical device 102 does not receive the keep-alive signal 106 within the specified time period, then at least a portion of the implantable medical device 102 is deactivated. Thus, in the event of an emergency or a malfunction, the user can deactivate at least a portion of the implantable medical device 102 by turning the remote device 104 off, which prevents the remote device 104 from transmitting, and the implantable medical device 102 from receiving, the keep-alive signal 106. Alternatively, the user or any other person can move the remote device 104 away from the implantable medical device 102 such that the implantable medical device 102 is outside the transmission range of the remote device 104.

The implantable medical device 102 is associated with the remote device 104 such that the implantable medical device 102 only recognizes keep-alive signals sent from the remote device 104. Associating the implantable medical device 102 with the remote device 104 prevents the implantable medical device 102 from receiving keep-alive signals transmitted from other remote devices in the vicinity of the implantable medical device 102.

The keep-alive signal 106 contains a signal identifier. The signal identifier matches a link identifier stored in the implantable medical device 102 in order for the implantable medical device 102 to properly receive the keep-alive signal 106. In one example, the signal identifier is unique to the remote device 104. In another example, the signal identifier is unique to the implantable medical device. In yet another example, the keep-alive signal 106 may include multiple signal identifiers associated with multiple implantable medical devices. In this example, at least one of the signal identifiers in the keep-alive signal 106 matches the link identifier stored in the implantable medical device 102 for the implantable medical device 102 to properly receive the keep-alive signal 106.

Figure 2:
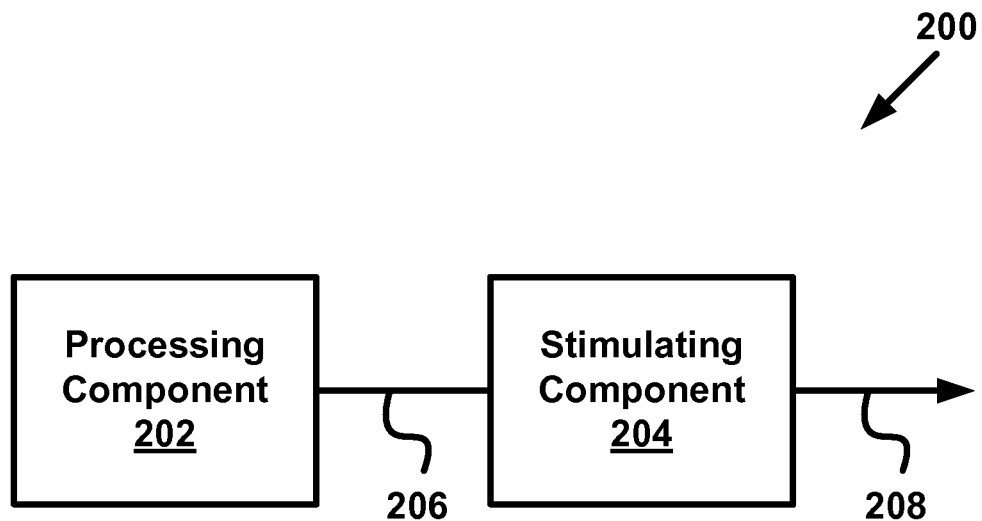
FIG. 2 is a block diagram of an implantable medical device depicted in FIG. 1, according to an example.

FIG. 2 is a block diagram of an implantable medical device 200. The implantable medical device 200 is one example of the implantable medical device 102 of the communication system 100. The implantable medical device 200 includes a processing component 202 and a stimulating component 204.

In one example, the implantable medical device 200 is a totally implantable medical device, such as a totally implantable cochlear implant or an implantable cardioverter-defibrillator. In this example, the processing component 202 and the stimulation component 204 are implanted in a user's body. In another example, the implantable medical device 200 is partially implantable, such as a conventional cochlear implant, a bone-conduction device, an auditory-brain-stem implant, a direct acoustic stimulation device, a hearing aid, and the like. When the implantable medical device 200 is partially implantable, at least a portion of the processing component 202 is externally attached to the user's body.

The processing component 202 includes components for receiving a stimulus. The processing component also includes components for processing the stimulus and sending an output signal to the stimulating component 204 via component link 206. The output signal includes information indicating how the stimulating component 204 stimulates an organ or body part of a user.

Figure 3:
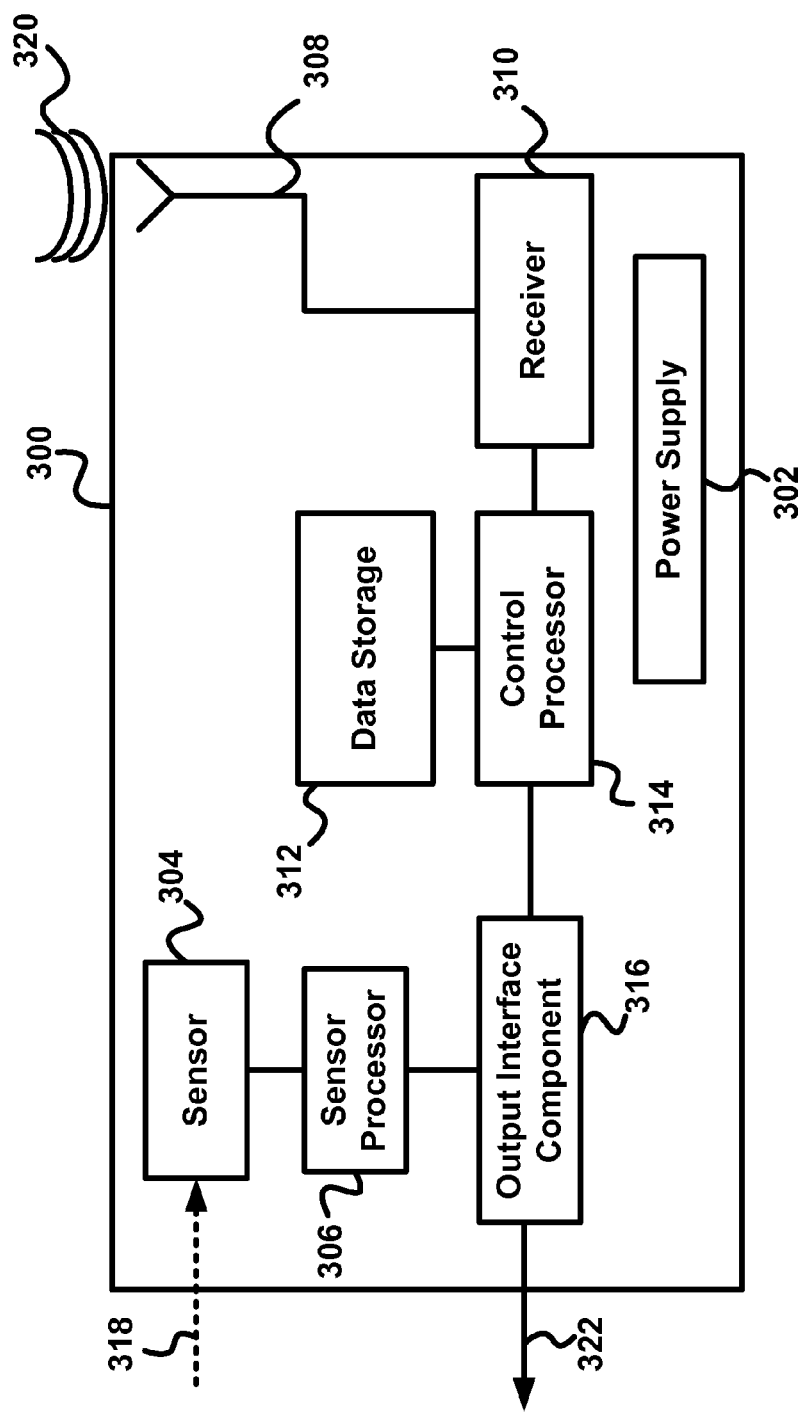
FIG. 3 is a block diagram of a processing component that may be part of the implantable medical device depicted in FIG. 2, according to an example.

FIG. 3 is a block diagram of a processing component 300. The processing component 300 includes a power supply 302, a sensor 304, a sensor processor 306, an antenna 308, a receiver 310, a data storage 312, a control processor 314, and an output interface component 316. The processing component 300 also includes additional bus work (not shown) and/or other electrical connections (not shown) connecting the components of the processing component 300. The processing component 300 is one example of the processing component 202 of the implantable medical device 200 depicted in FIG. 2.

The power supply 302 supplies power to various components of the processing component 300 and can be any suitable power supply, such as a non-rechargeable or rechargeable battery. In one example, the power supply 302 is a battery that can be charged wirelessly, such as through inductive charging. Such a wirelessly rechargeable battery reduces the need for access to the processing component to replace the battery, allowing for implantation of the processing component 300. In another example, the power supply 302 is not a replaceable or rechargeable battery and is configured to provide power to the components of the processing component 300 for the operational lifespan of the implantable medical device.

The sensor 304 receives a stimulus 318 and sends an input signal to the sensor processor 306 that includes information about the stimulus. In one example, the implantable medical device is a totally implantable cochlear implant. In this example, the sensor 304 is an omnidirectional microphone and the stimulus 318 is a sound. In another example, that implantable medical device may be a bone-conduction device, an auditory-brain-stem implant, a direct acoustic stimulation device, or the like. In this example, the sensor 304 is an omnidirectional microphone, a directional microphone, an electro-mechanical transducer, or any other audio transducer suitable for use in the type of hearing prosthesis employed. Furthermore, the sensor 304 includes one or more additional sensors.

The sensor processor 306 receives an input signal from the sensor 304. In one example, the sensor processor 306 is a digital signal processor and includes an analog-to-digital converter suitable for converting the input signal, which is an analog signal, into a digital input signal. In another example, the sensor processor 306 is any processor suitable for processing the input signal. The sensor processor 306 converts the input signal into a processed signal and sends the processed signal to the output interface component 316.

The antenna 308 receives a keep-alive signal 320 from a remote device, such as the remote device 104 of the communication system 100. In one example, the antenna 308 is configured to receive the keep-alive signal 320 in the radio frequency ("RF") spectrum, preferably in an industrial, scientific, and medical ("ISM") frequency band, such as a band from about 2.4 GHz to about 2.5 GHZ. In another example, the antenna 308 is configured to receive the keep-alive signal 320 in a different ISM band, such as a band from about 6.765 MHz to about 6.795 MHz, a band from about 13.553 MHz to about 13.567 MHz, a band from about 26.957 MHz to about 27.283 MHz, a band from about 40.660 MHz to about 40.700 MHz, a band from about 433.050 MHz to about 434.790 MHz, a band from about 863.000 MHz to about 870.000 MHz, a band from about 902.000 MHz to about 928.000 MHz, a band from about 5.725 GHz to about 5.875 GHz, a band from about 24.000 GHz to about 24.250 GHz, a band from about 61.000 GHz to about 61.500 GHz, a band from about 122.000 GHz to about 123.000 GHz, or a band from about 244.000 GHz to about 246.000 GHz. In still another example, the antenna 308 is configured to receive the keep-alive signal 320 at a frequency outside of the RF spectrum. Furthermore, in yet another example, the processing component 300 is configured to receive the keep-alive signal as an infrared signal, an ultrasonic signal, a magnetic signal, or any other similarly functioning signal. In this example, the processing component 300 includes a device capable of receiving the keep-alive signal 320 and may not include the antenna 308.

The receiver 310 receives the keep-alive signal 320 via the antenna 308. Additionally, the receiver 310 converts the keep-alive signal 320 into a converted keep-alive signal and sends the converted keep-alive signal to the control processor 314. In one example, the receiver 310 is configured to receive the keep-alive signal 320 in the RF spectrum, preferably a signal in an ISM frequency band, such as a band from about 2.4 GHz to about 2.5 GHz, though the receiver 320 may receive the keep-alive signal in a different ISM frequency band. In another example, the receiver 310 is configured to receive the keep-alive signal outside of the RF spectrum. Furthermore, in yet another example, the receiver 310 is configured to receive the keep-alive signal 320 as an infrared signal, an ultrasonic signal, a magnetic signal, or a signal in any other medium suitable for use in the communicating system 100.

The data storage 312 can be any type of non-transitory, tangible, computer readable media known or later developed configurable to store program code for execution by the processing component 300 and/or other data associated with the processing component 300. In one example, the data storage 312 stores a link identifier used by the control processor 314 for determining whether processing component 300 received the keep-alive signal. The data storage 312 also stores the current operating mode of the implantable medical device. In another example, the data storage 312 also stores information indicating a current setting of a parameter of the implantable medical device. For instance, when the implantable medical device is a hearing prosthesis, the data storage 312 stores information indicating a current volume setting for the implantable medical device.

The control processor 314 receives the converted keep-alive signal from the receiver 310 and determines the operating mode of the implantable medical device. In one example, the control processor 314 is configured to determine the operating mode of the implantable medical device upon receiving the converted keep-alive signal. In another example, the control processor 314 executes instructions for determining an operating mode of the implantable medical device 200. The data storage 312 stores the instructions for determining the operating mode of the implantable medical device 200, which may include instructions for implementing methods and processes disclosed herein, and the processor 314 accesses the instructions upon receiving the converted keep-alive signal. In determining the operating mode of the implantable medical device, the control processor 314 determines whether a signal identifier in the converted keep-alive signal matches the link identifier.

In one example, the implantable medical device operates in a normal operating mode, a safe operating mode, or a deactivated mode, though the implantable medical device may operate in more or fewer operating modes depending on the application. After determining the operating mode of the implantable medical device, the control processor 314 sends a control signal indicating the operating mode to the output interface component 316.

The output interface component 316 receives the control signal from the control processor 314 and the processed signal from the sensor processor 306. Additionally, the output interface component 316 sends an output signal 322 to a stimulation component of an implantable medical device, such as the stimulation component 204 of the implantable medical device 200 depicted in FIG. 2.

In one example, the control signal indicates that the operating mode of the implantable medical device is the normal operating mode. In this example, the output signal 322 includes the processed signal, though the output signal may include a parameter of an artificial stimulus based on the processed signal. In another example, the control signal indicates that the operating mode is the safe operating mode. In this example, the output signal 322 includes a portion of the processed signal or a parameter of the artificial stimulus based on a portion of the processed signal. In yet another example, the control signal indicates that the operating mode of the implantable medical device is the deactivated mode. In this example, the output interface component 316 does not send the output signal 322 to the stimulation component of the implantable medical device.

Returning to FIG. 2, the stimulating component 204 receives an output signal, such as the output signal 322 described in FIG. 3, from the processing component 202 via a component link 206. The stimulating component 204 also delivers an artificial stimulus 208 to an organ or a body part of a user of the implantable medical device 200. In one example, the implantable medical device 200 operates in the normal operating mode. The output signal includes a processed signal, such as the processed signal described in FIG. 3, and the stimulation component 204 utilizes the processed signal to deliver the artificial stimulus 208.

For example, consider a user with hearing loss. To alleviate this condition, the user utilizes the implantable medical device 200, which is a hearing prosthesis, such as a totally implantable cochlear implant. The processing component 202 receives a sound from an environment, processes the sound into the processed signal, and includes the processed signal in the output signal sent to the stimulating component 204 via the component link 206. The stimulating component 204 receives the output signal and converts the output signal into the artificial stimulus 208, which in this example is an electrical signal representing the sound. The stimulating component 204 delivers the artificial stimulus 208 to a region of the user's cochlea, thereby stimulating an auditory nerve and allowing the user to perceive the sound.

In another example, the implantable medical device 200 operates in a safe operating mode. In this example, the output signal includes a portion of the processed signal. For instance, when the implantable medical device 200 is a totally implantable cochlear implant, the output signal includes a portion of an amplitude of the processed signal. The stimulating component 204 receives the output signal and delivers the artificial stimulus 208 to the user's cochlea at a reduced current as compared to an artificial stimulus generated in the normal operating mode. This has the effect of reducing the amplitude (e.g., volume) of the sound perceived by the user.

In another example, the implantable medical device 200 is a hearing prosthesis. When the implantable medical device 200 operates in the safe mode, the output signal includes a certain frequency range of the processed signal. For instance, the output signal includes information from the processed signal inside a frequency range of about 60 Hz to about 7 kHz. The resulting artificial stimulus 208 allows the user to perceive a human voice, for example, but not a sound outside of the typical human voice range. In yet another example, a different frequency range is filtered from the processed signal based on the type of hearing loss experienced by the user.

In still another example, the implantable medical 200 device operates in the deactivated operating mode. In this example, the processing component 202 does not send the output signal to the stimulating component 204. Thus, the stimulating component 204 does not deliver the artificial stimulus 208 to the organ or the body part of the user.

Returning to FIG. 1, the remote device 104 may be worn on the user's body by using, for example, a clip or a strap, though the user does not need to wear the remote device 104 in order for the remote device 104 to function properly. The remote device 104 is a stand-alone electronic device that transmits the keep-alive signal. The remote device may also be configured to send an additional signal to and receive a signal from the implantable medical device 102. For example, the remote device 104 may also allow a user or a medical professional to receive a list of parameters from the implantable medical device 102 and send an adjustment of a parameter to the implantable medical device 102. For instance, if the implantable medical device 102 is a totally implantable cochlear implant, the user or the medical professional can adjust the sensitivity of an audio transducer.

The remote device 104 is configured to transmit the keep-alive signal 106 in the RF spectrum, preferably in an industrial, scientific, and medical ("ISM") frequency band, such as a band from about 2.4 GHz to 2.5 GHz. In another example, the remote device 104 transmits the keep-alive signal 106 outside of the RF spectrum, such as a low-frequency spectrum (e.g. <300 kHz). In yet another example, the remote device 104 transmits the keep-alive signal 106 as an ultrasonic signal, a loosely coupled magnetic induction signal, an infrared signal, or a signal in any other medium or form suitable for use in the communication system 100. Because the remote device is worn on the user's body, the remote device has a range of about 1 meter. In another example, the remote device may have a range up to about 10 meters.

The user of the implantable medical device 102 may wish to deactivate at least a portion of the implantable medical device 102 in certain situations, such as during an emergency or malfunction of the implantable medical device 102. However, since at least a portion of the implantable medical device 102 is implanted in the user's body, it is often impractical to quickly remove the implanted component(s). In one example, the remote device 104 provides the user with an interface for quickly deactivating at least a portion of the functionality of the implantable medical device 102. Interacting with the interface causes the remote device 104 to stop transmitting the keep-alive signal 106, thereby deactivating at least the portion of the implantable medical device 102.

Figure 4:
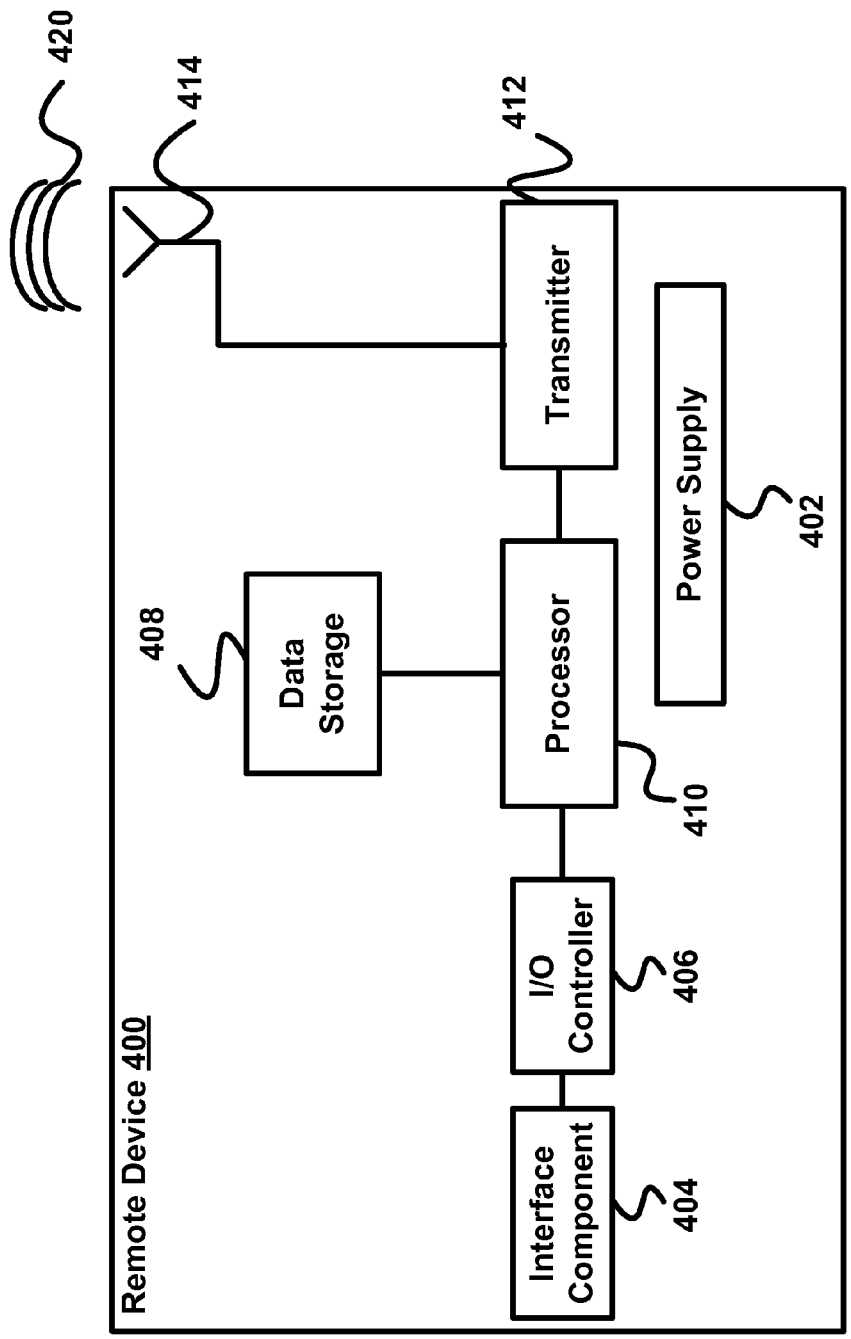
FIG. 4 is a block diagram of a remote device depicted in FIG. 1, according to an example.

FIG. 4 is a block diagram of a remote device 400. The remote device 400 is one example of the remote device 104 depicted in FIG. 1. The remote device 400 includes a power supply 402, an interface component 404, an I/O controller 406, a data storage 408, a processor 410, a transmitter 412, and an antenna 414. The remote device 400 also includes additional bus work (not shown) and/or other electrical connections (not shown) that connect the components of the remote device 400.

The power supply 402 is a battery capable of providing power to the remote device 400. In one example, the power supply 402 is replaceable. In another example the power supply 402 is integral to the remote device 400 and cannot be replaced. In this example, the power supply 402 is rechargeable or is designed to provide power to the remote device 400 for the duration of the lifespan of the remote device 400.

The interface component 404 includes an input interface, such as a switch or a button. The input interface is prominently displayed on the exterior of the remote device 400 and may include an identifying label, such as "Emergency Shut-off" In one example, it may be necessary to deactivate all or a portion of the implantable medical device during a medical emergency or malfunction of the implantable medical device. Furthermore, the user of the implantable medical device may be unable to interact with the interface component 404, such as in a situation where the user is unconscious. To facilitate deactivation of at least a portion of the implantable medical device during an emergency, the user or an emergency responder may operate the input interface of the interface component 404.

Activating the input interface of the interface component 404 results in the interface component 404 sending an input signal to the I/O controller 406. The I/O controller 406 receives the input signal from the interface component 404 and sends a shut-off signal to the processor 410. When the input interface of the interface component 404 is not activated, the interface component 404 does not send the input signal to the I/O controller 406. Likewise, the I/O controller 406 does not send the shut-off signal to the processor 410.

The data storage 408 is any type of non-transitory, tangible, computer readable media known or later developed configurable to store program code for execution by the remote device 400 and/or other data associated with the remote device 400. The data storage 408 may store a signal identifier that is included in a transmission of the keep-alive signal 420. In one example, the signal identifier is unique to the remote device 400. In another example, the signal identifier is unique to the implantable medical device. In yet another example, the data storage 408 stores multiple signal identifiers that are included in the keep-alive signal 420. For instance, the remote device 400 may be used to transmit the keep-alive signal 420 to multiple implantable medical devices. In this case, the data storage 408 stores an identifier for each of the multiple implantable medical devices.

The processor 410 determines the transmitting mode of the remote device 400. When the remote device 400 is on, the processor 404 sends a first signal to the transmitter 412 indicating that the transmitter 412 should transmit the keep-alive signal 420. Upon receiving the shut-off signal from the I/O controller 406, the processor 410 sends a second signal to the transmitter 412 indicating that the transmitter 412 should not transmit the keep-alive signal 420. In one example, the processor 410 includes a signal identifier in the first signal. In another example, the processor 410 includes multiple signal identifiers in the first signal, such as in a situation where the remote device 400 transmits the keep-alive signal 420 to multiple implantable medical devices.

The transmitter 412 is configured to transmit the keep-alive signal 420. In one example, the transmitter 412 transmits the keep-alive signal 420 in the RF spectrum, preferably in an ISM frequency band, such as a band from about 2.4 GHz to about 2.5 GHz, though the transmitter 412 may transmit the keep-alive signal 420 in a different ISM frequency band. In another example, the transmitter 412 transmits the keep-alive signal 420 in the low frequency spectrum. In yet another example, the transmitter 412 transmits the keep-alive signal 420 as an infrared signal, an ultrasonic signal, a magnetic signal, or a signal in any other form or medium suitable for transmitting the keep-alive signal 420 to the implantable medical device.

The transmitter 412 also receives one of the first signal and the second signal from the processor 410. When the transmitter 412 receives the first signal, the transmitter 412 transmits the keep-alive signal 420 in a normal transmitting mode. In one example, the transmitter 412 transmits the keep-alive signal 420 at a first transmission rate when in the normal transmitting mode. For instance, if the transmission rate is one transmission every 1 msec, the transmitter 412 transmits the keep-alive signal once every 1 msec. In another example, the first transmission rate is any rate suitable for ensuring the implantable medical device operates in the normal operating mode. The transmitter 412 continues transmitting the keep-alive signal 420 at the first transmission rate until the transmitter 412 receives the second signal from the processor 410.

When the transmitter 412 receives the second signal from the processor 410, the transmitter 412 does not transmit the keep-alive signal 420 in the normal transmitting mode. In one example, when the transmitter 412 receives the second signal from the processor 410, the transmitter 412 does not transmit the keep-alive signal 420 until the transmitter 412 receives the first signal from the processor, indicating that input interface of the interface component 404 is no longer activated.

Alternatively, the transmitter 412 transmits the keep-alive signal 420 in a safe transmitting mode. In one example, the safe transmitting mode includes a cycle in which the transmitter 412 transmits the keep-alive signal 420 during an on interval and does not transmit the keep-alive signal during an off interval. During the on interval, the transmitter 412 transmits the keep-alive signal at the first transmission rate. For instance, the first transmission rate is one transmission every 1 msec, the on interval is 20 msec, and the off interval is 20 msec. Thus, the transmitter 412 transmits the keep-alive signal 420 once every 1 msec for 20 msec and does not transmit the keep-alive signal during the off interval. The transmitter 412 repeats the cycle until the transmitter 412 receives the first signal from the processor 410, indicating that input interface of the interface component 404 is no longer activated.

In another example, the transmitter 412 transmits the keep-alive signal at a second transmission rate when in the safe transmitting mode. Transmitting at the second transmission rate results in fewer transmissions of the keep-alive signal 420 during a time period than transmitting at the first transmission rate during the time period. For example, if the first transmitting rate is one transmission every 1 msec, the second transmission rate is one transmission every 2 msec. The transmitter 412 continues transmitting the keep-alive signal 420 at the second transmission rate until the transmitter 412 receives the first signal from the processor 410.

The transmitter 412 may also include a signal identifier in each transmission of the keep-alive signal 420. In one example, the signal identifier is stored in the data storage 408, and the processor 410 includes the signal identifier in the first signal. In another example, the signal identifier is not stored in the data storage 408 and the first signal does not include the signal identifier. In this example, the transmitter 412 is configured to include the signal identifier in the keep-alive signal 420. In yet another example, the transmitter 412 includes multiple signal identifiers in the keep-alive signal. In this example, the transmitter 412 receives the multiple identifiers from the processor 410 in the first signal. Alternatively, the transmitter 412 is configured to include each of the multiple identifiers in the keep-alive signal 420.

The antenna 414 is configured to transmit the keep-alive signal 420. In one example, the antenna 414 is configured to transmit the keep-alive signal 420 in the RF spectrum, preferably in an ISM frequency band, such as a band of about 2.4 GHz to about 2.5 GHz. In another example, the antenna 414 is configured to transmit the keep-alive signal in the low frequency spectrum. In yet another example, the transmitter 412 transmits the keep-alive signal 420 as an electro-magnetic signal. In this example, the antenna 414 is replaced with a component suitable for transmitting the keep-alive signal 420.

Figure 5:
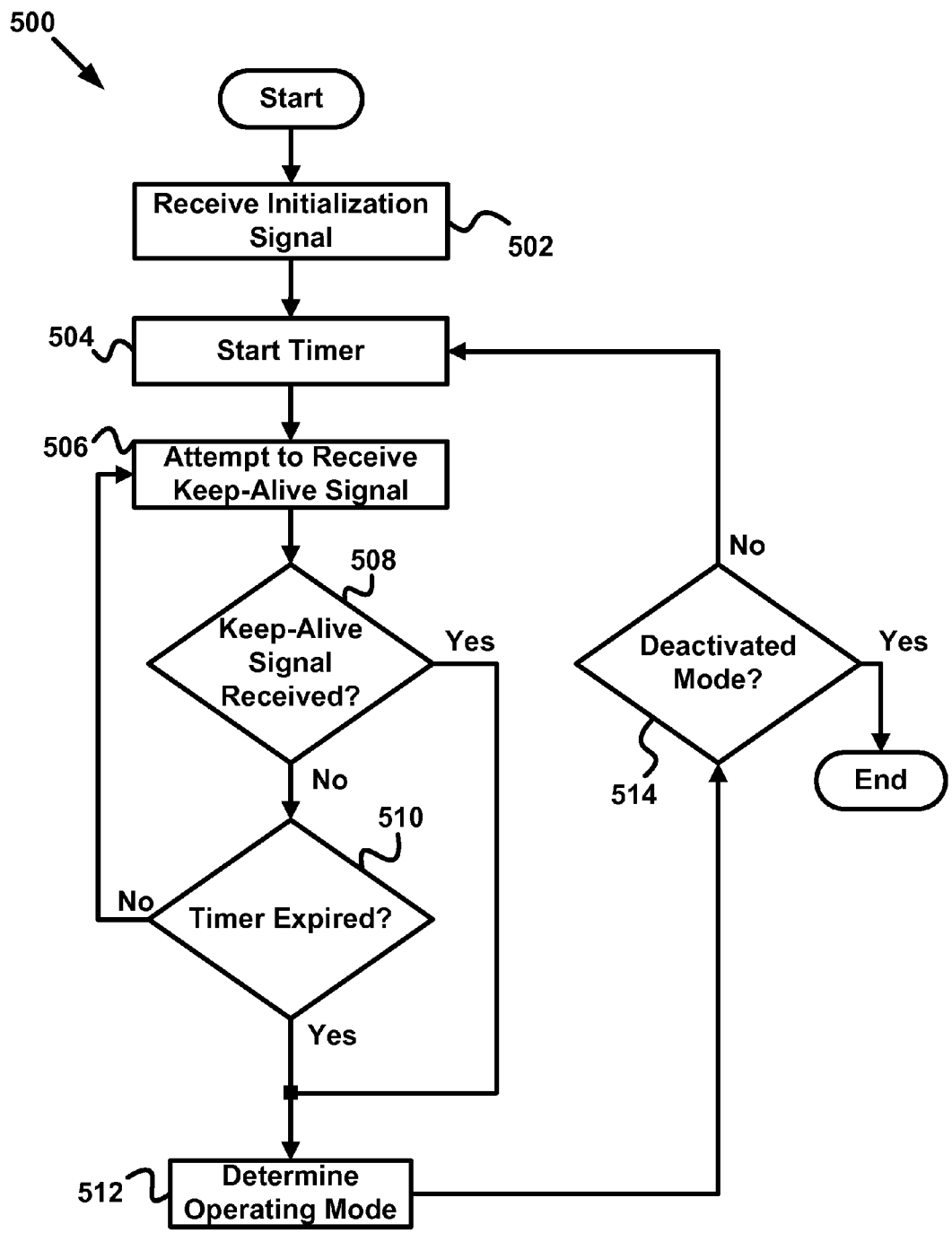
FIG. 5 is a flow diagram of a method for determining if a keep-alive signal is received at an implantable medical device, according to an example.

FIG. 5 is a flow diagram of a method 500. The method 500 allows a component of an implantable medical device to determine whether the implantable medical device received a keep-alive signal. While the processing component 300 and the remote device 400 are used for purposes of describing the method 500, it is understood that other devices may be used.

The method 500 may include one or more operations, functions, or actions as illustrated in blocks 502-516. Although the blocks are illustrated in sequential order, these blocks may be performed in parallel and/or in a different order than those described herein. Also, the various blocks may be combined into fewer blocks, divided into additional blocks, and/or removed based upon the desired implementation.

In addition, for the method 500 and other processes and methods disclosed herein, the flow diagram shows functionality and operation of one possible implementation of one example. In this regard, each block may represent a module, a segment, or a portion of program code, which includes one or more instructions executable by a process for implementing specific logical functions or steps in the process. The program code may be stored on any type of computer readable medium, such as a storage device including a disk or hard drive, for example. The computer readable medium may include non-transitory computer readable media, such as a computer readable media that stores data for a short period of time, such as register memory, processor cache, or Random Access Memory ("RAM"). The computer readable medium may also include non-transitory computer readable media suitable as secondary or persistent long term storage, such as read-only memory ("ROM"), optical or magnetic discs, compact-disc read-only memory ("CD-ROM"), or the like. The computer readable medium may also include any other volatile or non-volatile storage systems. The computer readable medium may be considered computer readable storage medium, for example, or a tangible storage device.

In addition, for the method 500 and other processes and methods discussed herein, each block of FIG. 5 may represent circuitry that is wired to perform the specific logical functions of the process.

At block 502, the processing component 300 receives an initialization signal. In one example, the initialization signal is the keep-alive signal 320 sent from the remote device 400. In this example, the receiver 310 receives the initialization signal via the antenna 308 and converts the initialization signal into a converted initialization signal. The receiver 310 sends the converted initialization signal to the control processor 314, and the control processor 314 determines whether the signal identifier included in the converted initialization signal matches the link identifier stored in the data storage 312. Upon determining that the signal identifier matches the link identifier, the control processor 314 sends a control signal to the output interface component 316 indicating the operating mode as the normal operating mode. In another, example the control signal indicates that the operating mode is an operating mode other than the normal operating mode, such as the safe operating mode.

In still another example, the processing component 300 receives the initialization signal from an additional remote device. The receiver 310 may receive the initialization signal via the antenna 308 and may send a converted initialization signal to the control processor 314. Alternatively, the control processor 314 receives the converted initialization signal from another component (not shown) of the processing component 300. In this example, the converted initialization signal includes the operating mode of the implantable medical device, which the control processor 314 includes in the control signal.

At block 504, the control processor 314 commences a cycle for receiving the keep-alive signal 320 by starting a timer. The timer represents a period of time in which the processing component 300 receives the keep-alive signal 320. In one example, the timer is set at about 2 msec, though in another example the period of time is as long as about 24 hours or even longer.

At block 506, the processing component 300 receives the keep-alive signal 320. The receiver 310 receives the keep-alive signal 320 via the antenna 308. The receiver 310 converts the keep-alive signal 320 into the converted keep-alive signal and sends the converted keep-alive signal to the control processor 314.

At block 508, the control processor 314 executes instructions for determining whether the keep-alive signal 320 was received. Included in this determination is determining whether at least one signal identifier in the converted keep-alive signal matches the link identifier stored in the data storage 312. If the control processor 314 determines that at least one signal identifier in the converted keep-alive signal matches the link identifier, the control processor 314 determines that the processing component 300 received the keep-alive signal 320, and the control processor 314 determines the operating mode of the implantable medical device at block 512.

At block 510, the control processor 314 determines if the timer has expired upon determining that the processing component 300 did not receive the keep-alive signal 320 at block 508. If the time has not expired, the processing component 300 may still receive the keep-alive signal 320 in the current cycle. Thus, the processing component 300 reattempts to receive the keep-alive signal 320 at block 506. If the timer has expired at block 510, the control processor 314 determines the operating mode of the implantable medical device.

At block 512, the control processor 314 determines the operating mode of the implantable medical device. In one example, the control processor 314 may determine the operating mode by executing instructions capable of implementing the method 600 described with reference to FIG. 6. In another example, the control processor 314 executes any set of instructions suitable for determining the operating mode of the implantable medical device.

Figure 6:
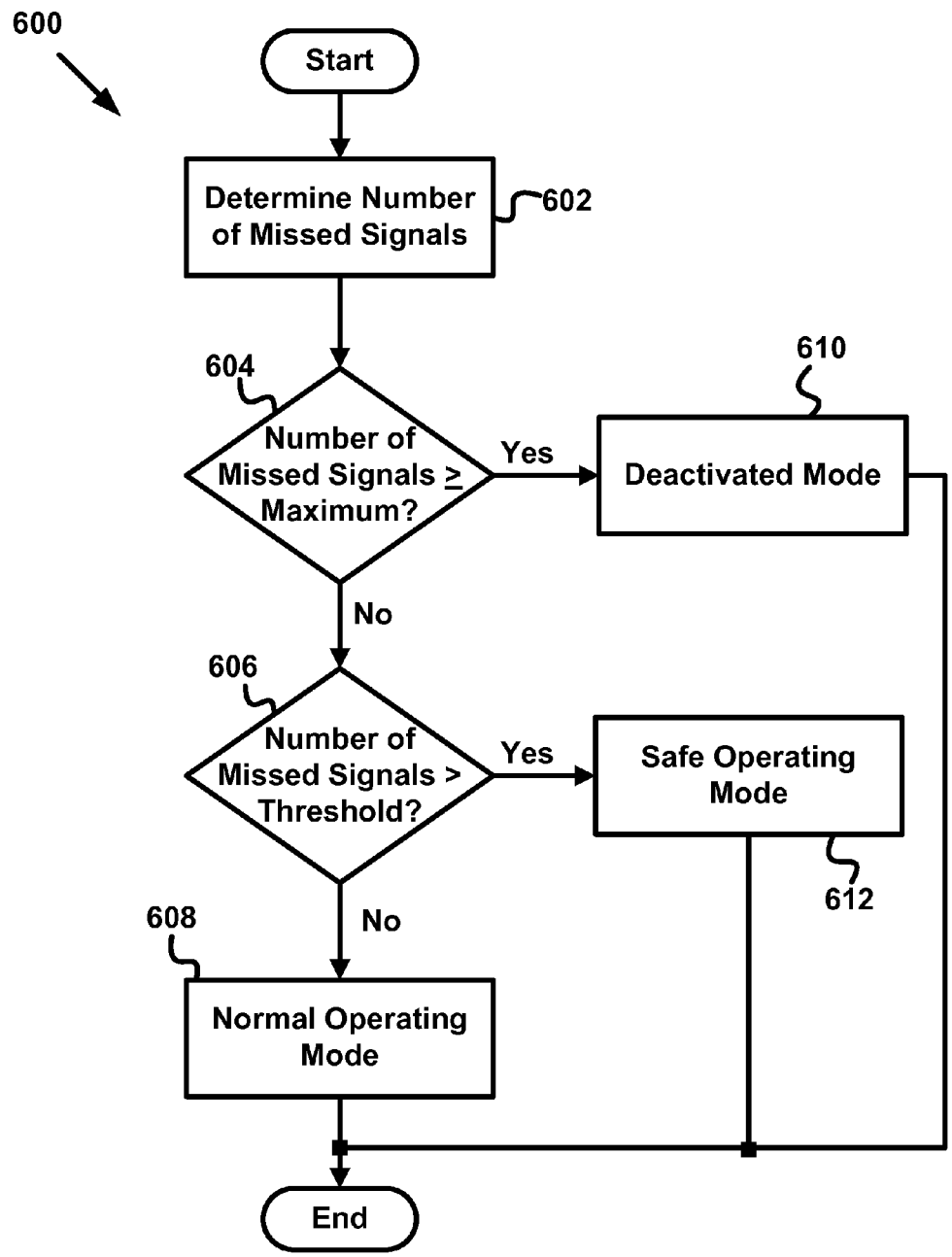
FIG. 6 is a flow diagram of a method for determining an operating mode of an implantable medical device, according to an example.

FIG. 6 is a flow diagram of a method 600. The method 600 allows a component of an implantable medical device to determine the operating mode of the implantable medical device. While the processing component 300 is used for purposes of describing the method 600, it is understood that other devices may be used. The method 600 may include one or more operations, functions, or actions as illustrated in blocks 602-612. Although the blocks are illustrated in sequential order, these blocks may be performed in parallel and/or in a different order than those described herein. Also, the various blocks may be combined into fewer blocks, divided into additional blocks, and/or removed based upon the desired implementation.

At block 602, the control processor 314 determines a number of missed signals. The number of missed signals represents the number of cycles—such as the cycle beginning at block 504 in the method 500—in which the processing component 300 did not receive keep-alive signal 320 in a sample interval, where the sample interval is an integer number of cycles. In one example, the sample interval is the last twenty cycles for receiving the keep-alive signal 320. In another example the sample interval is a number of cycles that may be greater than or less than twenty. The data storage 312 may store number of missed signals and the sample interval.

At block 604, the control processor 314 compares the number of missed signals to a maximum number of missed signals. The maximum number of missed signals represents the maximum allowable number of cycles in which the processing component 300 does not receive the keep-alive signal 320 and continues to operate. In one example, the maximum number of missed signals is fifteen, though the maximum number of missed signals may be any integer less than or equal to the time interval. If the number of cycles is less than the maximum number of missed signals, the control processor 314 compares the number of missed signals to a threshold number of missed signals, at block 606. If the number of missed signals is greater than or equal to the maximum number of missed signals, then the control processor 314 determines that the operating mode of the implantable medical device is the deactivated mode, at block 610.

The number of missed signals may be greater than or equal to the maximum number of missed signals in several circumstances. In one example, with reference to FIG. 1, an individual may turn the remote device 104 off. Alternatively, the user or an emergency responder activates an emergency shut-off component of the remote device 104, such as the interface component 404 described in FIG. 4, causing the remote device 104 to cease transmitting the keep-alive signal 106. In either case, the remote device 104 no longer transmits the keep-alive signal 106, preventing the implantable medical device 102 from receiving the keep-alive signal 106.

In another example, if the implantable medical device 102 is outside of the transmission range of the remote device 104, the implantable medical device 102 cannot receive the keep-alive signal 106. For example, the timer (as discussed above with respect of method 500) is set at about 2 msec and the maximum number of missed signals is fifteen. In this example, if the implantable medical device 102 is outside the range of the remote device 104 for about 30 msec or longer in about a 40 msec period, the number of missed signals will generally be greater than or equal to the maximum number of missed signals.

Comparing the number of missed signals to the maximum number of missed signals accounts for potential errors in the implantable medical device receiving the keep-alive signal. However, in one example, the user may wish to deactivate the component link as soon as a keep-alive signal is missed. In this example, the maximum number of missed signals is one, and the control processor 314 determines that the operating mode of the implantable medical device is the deactivated mode as soon as the processing component 300 fails to receive the keep-alive signal 320 in a given time interval.

Returning to FIG. 6, at block 606, the control processor 314 compares the number of missed signals to the threshold number of missed signals. The threshold number of missed signals represents an allowable number of cycles in which the processing component 300 does not receive the keep-alive signal and continues to operate in a normal operating mode. In one example, the threshold number of missed signals is five, though in another example the threshold number of missed signals is any integer less than maximum number of missed signals. For instance, if the maximum number of missed cycles is fifteen, the threshold number of missed signals can be any number less than fifteen.

If the number of missed signals is greater than the threshold number of missed signals, then the control processor 314 determines that the operating mode of the implantable medical device is the safe operating mode, at block 612. Otherwise, the control processor 314 determines that operating mode of the implantable medical device is the normal operating mode, at block 608.

In one example, the implantable medical device is not configured to operate in the safe operating mode. In this example, the implantable medical device does not execute block 606 of method 600, and the implantable medical device continues operating in the normal operating mode as long as the number of missed signals is less than the maximum number of missed signals. In another example, the implantable medical device continues operating regardless of the number of missed signals. In this example, the implantable medical device does not perform block 604 of the method 600.

Returning to FIG. 5, at block 514, the control processor 314 determines whether the operating mode of the implantable medical device is the deactivated mode. If the control processor 314 determines that the operating mode is not the deactivated mode, the cycle recommences at block 504. If the control processor 314 determines that the operating mode of the implantable medical device is the deactivated mode, the method 500 ends. When the implantable medical device operates in the deactivated mode, conditions exist such that the processing component 300 cannot receive the keep-alive signal 320. In order to restore a deactivated portion of the implantable medical, the implantable medical device receives an initialization signal, thereby reinitiating the method 500.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
receiving at a hearing prosthesis a first transmission of a signal;
starting a timer for an interval of time in which to receive a second transmission of the signal;
determining whether the hearing prosthesis received the second transmission of the signal prior to an expiration of the timer;
in response to determining that the hearing prosthesis received the second transmission of the signal prior to the expiration of the timer, delivering a first stimulus to a body part of a recipient; and
in response to determining that the hearing prosthesis failed to receive the second transmission of the signal prior to the expiration of the timer, delivering a second stimulus to the body part, wherein
a current of the first stimulus is greater than a current of the second stimulus; and
the first stimulus and the second stimulus cause the recipient to perceive at least a portion of a sound.

2. The method of claim 1, wherein receiving the first transmission of the signal activates the hearing prosthesis.

3. The method of claim 1, wherein the signal includes a signal identifier.

4. The method of claim 3, further comprising:
determining that the signal identifier contained in the first transmission of the signal matches a link identifier, unique to the hearing prosthesis; and
activating the hearing prosthesis upon determining that the signal identifier matches the link identifier.

5. The method of claim 3, wherein determining that the hearing prosthesis failed to receive the second transmission of the signal prior to the expiration of the timer includes determining that the signal identifier contained in the second transmission of the signal and a link identifier unique to the hearing prosthesis are different.

6. The method of claim 1, further comprising:
determining a number of consecutive intervals in which the hearing prosthesis failed to receive a second transmission of the signal;
determining whether the number exceeds a threshold value; and
in response to determining that the number exceeds the threshold value, deactivating a stimulation component of the hearing prosthesis that delivers the first stimulus and the second stimulus to the body part.

7. A method comprising:
determining a number of missed signals in a sample interval, wherein the number of missed signals includes a first number of time intervals in which a hearing prosthesis configured to stimulate a body part of a recipient to cause a recipient to perceive a portion of a sound failed to receive a signal, and wherein the sample interval comprises a second number of time intervals in which the signal could have been received;
making a first determination that includes determining whether the number of missed signals is less than a first value that represents a first allowable number of time intervals in which the hearing prosthesis failed to receive the signal; and
selecting an operating mode of the hearing prosthesis implantable medical device based on the first determination, wherein a maximum amplitude of a stimulus delivered by the hearing prosthesis to the body part depends on the operating mode.

8. The method of claim 7, wherein the operating mode is at least one of:
a normal operating mode, wherein the maximum amplitude of the stimulus is a first maximum amplitude in the normal operating mode;
a safe operating mode, wherein the maximum amplitude of the stimulus is a second maximum amplitude in the safe operating mode, wherein the second maximum amplitude is less than the first maximum amplitude; and
a deactivated mode, wherein the maximum amplitude of the stimulus is zero in the deactivated mode.

9. The method of claim 8, further comprising sending an output signal to a component of the hearing prosthesis, wherein the output signal indicates the operating mode of the hearing prosthesis.

10. The method of claim 8, wherein the operating mode of the hearing prosthesis is the normal operating mode when the first determination indicates that the number of missed signals is less than the first value.

11. The method of claim 8, wherein the operating mode of the hearing prosthesis is the deactivated mode when the first determination indicates the number of missed signals is greater than or equal to the first value.

12. The method of claim 8, wherein the operating mode of the hearing prosthesis is the safe operating mode when the first determination indicates that the number of missed signals is greater than or equal to the first value.

13. The method of claim 8, further comprising:
making a second determination that includes determining whether the number of missed signals is less than a second value that represents a second allowable number of time intervals in which the hearing prosthesis failed to receive the signal, wherein the second value is less than the first value.

14. The method of claim 13, wherein the operating mode of the hearing prosthesis is the normal operating mode when the second determination indicates that the number of missed signals is less than the second value.

15. The method of claim 13, wherein the operating mode of the hearing prosthesis is the safe operating mode when the first determination indicates that the number of missed signals is less than the first value and the second determination indicates that the number of missed signals is greater than or equal to the second value.

16. The method of claim 13, wherein the operating mode of the hearing prosthesis is the deactivated mode when the first determination indicates that the number of missed signals is greater than or equal to the first value.

17. A system comprising:
a remote device configurable to transmit a signal; and
a hearing prosthesis configured to receive the signal within in a time interval, wherein in response to the hearing prosthesis failing to receive the signal within the time interval, a component of the hearing prosthesis reduces amplitudes of stimuli delivered to a recipient that cause the recipient to perceive at least a portion of a sound.

18. The system of claim 17, wherein the remote device includes an input component, and wherein the remote device is further configurable to stop transmitting the signal upon activation of the input component.

19. The system of claim 17, wherein the hearing prosthesis is deactivated upon the hearing prosthesis failing to receive the signal more than a threshold number of times in a monitoring interval, wherein the monitoring interval is longer than the time interval.

20. The system of claim 17, wherein the transmission range of the remote device ranges from about 1 meter to about 10 meters.

21. The system of claim 17, wherein the remote device is further configurable to include at least one identifiers in the signal, and wherein a link identifier is stored in a data storage of the hearing prosthesis.

22. The system of claim 21, wherein the hearing prosthesis is further configurable to determine whether at least one of the at least one identifiers in the signal matches the link identifier, wherein the hearing prosthesis fails to receive the signal upon determining that none of the at least one identifiers in the signal match the link identifier.

23. The system of claim 22, wherein the link identifier is unique to the remote device.

24. The system of claim 22, wherein the identifier is unique to the hearing prosthesis.

25. A device comprising:
   a sensor configured to receive a sound from an environment;
   a sound processor configured to receive a sensor output from the sensor and generate a processed signal based on the sensor output;
   a stimulating component configured to generate a stimulus that stimulates a body part associated with auditory perception in a human body;
   an output component configured to send an output signal to the stimulating component, wherein the output signal includes information used to generate the stimulus;
   a receiver configured to receive a first signal from a remote device; and
   a processor configured to:
      determine whether the receiver received the first signal within a first time interval;
      send a first control signal to the output component in response to determining that the receiver received the signal within the first time interval, wherein the first control signal causes the output component to include the processed signal in the output signal; and
      send a second control signal to the output component in response to determining that the receiver failed to receive the signal within the first time interval, wherein the second control signal causes the output component to include a portion of the processed signal in the output signal.

26. The device of claim 25 further comprising an antenna, wherein the receiver is configured to receive the first signal via the antenna, and wherein the antenna and the receiver are configured to receive the signal in an industrial, scientific, and medical frequency band.

27. The device of claim 25, wherein including the portion of the processed signal in the output signal causes the stimulation component to generate a stimulus having a lower current than a stimulus generated using the processed signal.

28. The device of claim 25, wherein the processor is further configured to:
   determine whether the receiver received the first signal within a second time interval, wherein the second time interval is longer than the first time interval; and
   send a third control signal to the output component in response to determining that the receiver failed to receive the first signal within the second time interval, wherein the third control signal causes the output component to stop sending the output signal to the stimulating component.

* * * * *